United States Patent
Wicks et al.

(10) Patent No.: US 6,699,847 B2
(45) Date of Patent: Mar. 2, 2004

(54) ANTIPARASITIC FORMULATION

(75) Inventors: Stephen Richard Wicks, Kent (GB); Timothy Michael Lukas, Kent (GB); Valerie Denise Harding, Kent (GB); Snezana Milojevic, Kent (GB)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 10/039,608

(22) Filed: Nov. 7, 2001

(65) Prior Publication Data

US 2002/0142972 A1 Oct. 3, 2002

Related U.S. Application Data

(63) Continuation of application No. 09/459,192, filed on Dec. 10, 1999, now abandoned.

(30) Foreign Application Priority Data

Dec. 16, 1998 (GB) .............................. 9827727

(51) Int. Cl.⁷ ..................... A61K 31/715; A61K 31/70
(52) U.S. Cl. ........................................... 514/53; 514/25
(58) Field of Search ..................... 514/53, 25

(56) References Cited

U.S. PATENT DOCUMENTS

| | | | | |
|---|---|---|---|---|
| 5,580,574 A | | 12/1996 | Behl et al. ................... | 424/449 |
| 6,063,394 A | * | 5/2000 | Grosse-Bley et al. ....... | 424/422 |
| 6,174,540 B1 | | 1/2001 | Williams et al. ............ | 424/423 |

FOREIGN PATENT DOCUMENTS

| | | | |
|---|---|---|---|
| CA | 1237672 | 12/1983 | |
| EP | 0140255 | 5/1985 | |
| EP | 0211691 | 2/1987 | |
| EP | 0393890 | 10/1990 | |
| EP | 0413538 | 2/1991 | |
| EP | 0535734 | 4/1993 | |
| GB | 1126892 | 9/1968 | |
| WO | WO9526291 | 10/1995 | |
| WO | WO9711709 | 4/1997 | |
| WO | WO9737653 | 10/1997 | .......... A61K/31/35 |
| WO | WO9811902 | 3/1998 | |

OTHER PUBLICATIONS

M. Ash, et al.; Gower Publishing Ltd.; Handbook of Pharmaceutical Additives; pp395 (1995).

A. J. Spiegel, et al.; Use of Nonaqueous Solvents in Paranteral Products; J. Pharm. Sciences; vol. 52, No. 10 pp 917–927 (1963).

R. Deanesly, et al.; Note on the subcutaneous absorption of oils by rats and mice, with special reference to the assay of cestrin; Nat. Inst. For Medical Research, London; vol. 78 pp 155–160 (1933).

George J. Brewer, et al.; Parenteral Depot Method for Zinc Administration; J. Pharmacology; vol. 23: pp 254–263 (1981).

Mary–Anne Mackey, et al.; Tolerability of Intramuscular Injections of Tesosterone Ester in Oil Vehile; Human Reproduction; vol. 10 No. 4, pp 862–865 (1995).

* cited by examiner

*Primary Examiner*—Theodore J. Criares
*Assistant Examiner*—Jennifer Kim
(74) *Attorney, Agent, or Firm*—Peter C. Richardson; Gregg C. Benson; Lance Y. Liu

(57) ABSTRACT

Long-acting antiparasitic formulations of doramectin, suitable for injection, are described herein.

6 Claims, No Drawings

ANTIPARASITIC FORMULATION

This Application is a continuation of Ser. No. 09/459,192 filed Dec. 10, 1999, now abandon.

FIELD OF THE INVENTION

This invention relates to long-acting antiparasitic formulations containing doramectin, suitable for parenteral administration, e.g. by subcutaneous or intramuscular injection to animals such as cattle, sheep, swine, etc., and which are useful in the treatment of conditions caused by endo- and/or ectoparasites.

BACKGROUND OF THE INVENTION

Doramectin (the active ingredient in Dectomax™) is a potent parasiticide sparingly soluble in water, described by AC Goudie et al, in *Vet. Parasitol.* 49(1) (July 1993). Injectable formulations of doramectin in sesame oil/ethyl oleate were disclosed in EP 0 393 890, and discussed by S R Wicks et al, in *Vet. Parasitol.* 49(1) (July 1993). Doramectin is effective in the treatment of parasites such as those mentioned in the above publications, herein incorporated by reference in their entirety. Such parasites can harm livestock animals and can cause severe economic losses.

Long acting injectable formulations of avermectins in hydrophobic carriers and small amounts of hydrogenated castor oil were disclosed in EP 0 535 734, and in triacetin in EP 0 413 538.

SUMMARY OF THE INVENTION

We have now discovered formulations of doramectin which have long duration of action in vivo, and which have beneficial properties e.g. injection site tolerability, stability on storage, acceptable viscosity, syringeability across a wide temperature range, and good bioavailability. The relatively high levels of doramectin possible in these formulations enables administration of low volumes of formulation, without loss of the beneficial properties mentioned above.

According to the invention there are provided formulations comprising doramectin at about 1–11% w/v, in a solvent comprising castor oil at about 25–80% v/v and either
(i) ethyl oleate at about 20–75% v/v, or
(ii) fractionated coconut oil at about 20–75% v/v, and
(iii) optional further auxiliaries.

DETAILED DESCRIPTION OF THE INVENTION

Castor oil is the fixed oil obtained from the seed of *Ricinus communes* L. (fam. Euphorbiaceae). It is a clear, almost colourless or slightly yellow, viscid liquid. See e.g. USP 23 and Ph.Eur.—Official Monographs. There are various commercial sources of this material. It has long been known as an ingredient in parenteral, i.e. injection formulations (e.g. see Martindale—the Extra Pharmacopoeia, The Royal Pharmaceutical Society, 30th edition; Encycopaedia of Pharmaceutical technology, vol 8, ed. J Swarbrick and J C Boylan, 1993, Marcel Dekker; Handbook of Pharmaceutical Additives, p.395, M. Ash et al, Gower Publishing Ltd. 1995; A J Spiegel and M M Noseworthy, J. Pharm. Sci, October 1963, vol.52, no.10, 917; European Patent Application publication no. 0 140 255 A2 (Sumitomo); R Deansly et al, J. Physiol., 78, 155, 1933; G J Brewer et al, Pharmacology (1981) 23:254; M-A Mackey et al, Human Reproduction, vol. 10, no.4, 862 (1995); British Patent 1,126,892 (Schering); European Patent Application publication no.0 211 691 A2 (Eli Lilly and Co.); Canadian Patent 1 237 672 (Bayer Aktiengesellschaft); International Patent Application publication number WO 95/26291 (Boehringer Ingelheim); etc.). Injection formulations based on castor oil have been commercialised for a number of drug substances, for example the immunosuppressant macrolide tacrolimus (Prograf/Fujiswawa, FK-506).

Ethyl oleate [CAS no.: 111-62-6] is available commercially, for example from Croda Oleochemicals. The commercial product is a pale yellow oil with a maximum acid value of 0.5 mgKOH/g, an ester value of 100–105%, an iodine value of 75–85 g/100 g, specific gravity of 0.866–0.874 kg/l at 25 degrees centigrade, and may sometimes contain an antioxidant such as butylhydroxyanisole (BHA) at approximately 0.01%.

By "fractionated coconut oil" is meant the fraction of coconut oil containing propylene glycol octanoic/decanoic diester, with typical C6 fatty acid content of at most ca. 3%, C8 approximately 65–80%, C10 approximately 10–30% and C12 at most 3%, an acid number of at most 0.1, saponification number of approx. 320 to 340 and an iodine number of at most 1, or a reconstituted mixture having substantially the same composition as said fraction. An example of the fractionated coconut oil which can be used in the formulations according to the invention is sold under the name Miglyol™ 840 (Huls).

The formulations of the invention are useful in the treatment of economically important parasite infections, including endo-parasites such as gastrointestinal roundworms, i.e. nematodes (e.g. Cooperia sp.), lungworms (*Dictyocaulus viviparus*), and other endo-parasites mentioned in EP 0 393 890. The formulations are also useful in the treatment of ecto-parasites such as arthropods such as ticks, mites, lice, fleas, blowfly, biting insects, migrating dipterous larvae, etc.

Formulations within the scope of the invention have been shown to provide efficacy against economically important endo-parasites at up to 4 months, and ecto-parasites at up to 3 months, following a single injection. This represents a significant advantage for those working in the field of livestock animals as it offers effective treatment with one application per season.

One preferred group of formulations is where the castor oil is present in the solvent at about 55–75% v/v.

Preferably the amount of doramectin is 3–9% w/v, more preferably about 5–9% w/v, and most preferably about 6% w/v of the total formulation.

Preferably the solvent is selected from castor oil/ethyl oleate (from 2:3 v/v to 2:1 v/v, especially 2:3 v/v to 3:2 v/v) and castor oil/fractionated coconut oil (from 2:7 v/v to 4:7 v/v).

Optionally the formulations may contain further auxiliaries generally used in pharmaceutical or veterinary injectable formulations in small amounts, such as a free radical scavenger antioxidant e.g. BHA, a preservative such as phenol, m-cresol, etc.

Preferred specific formulations are those mentioned in the Examples below, especially those of Examples 1, 2, 3, 1A, 2A, 3A, 1B, 2B, 3B, 1C, 2C and 3C.

Another aspect of the invention is a method of treatment of a condition caused by an endo- or ectoparasite by administration of an effective amount of a formulation according to the invention.

Another aspect of the invention is a formulation according to the invention for use in medicine.

Another aspect of the invention is the use of a formulation according to the invention in the manufacture of a medicament for the treatment of conditions caused by endo- or ecto-parasites.

Formulations according to the invention can be made by standard methods, in accordance with standard pharmaceutical or veterinary practice. For example the doramectin (and optional other constituents) can be dissolved in the solvent mixture, sterilised and packed in a manner well-known in the art.

The invention is illustrated by the following examples, wherein "FCO" is fractionated coconut oil [Miglyol™ 840 (Huls)], and "EO" is ethyl oleate.

EXAMPLES

| Ex. | % w/v doramectin | % castor oil v/v(solvent) | % FCO/EO v/v (solvent) |
|---|---|---|---|
| 1 | 6 | 60 | 40(EO) |
| 2 | 6 | 40 | 60(EO) |
| 3 | 6 | 30 | 70(FCO) |
| 4 | 3 | 40 | 60(EO) |
| 5 | 9 | 60 | 40(EO) |
| 6 | 3 | 30 | 70(EO) |
| 7 | 6 | 70 | 30(EO) |

Further examples 1A-7A are in accordance with the constituents of Examples 1–7 above with BHA antioxidant also present, at 0.1%w/v.

Yet further examples 1B-7B are in accordance with the constituents of Examples 1–7 above with BHA antioxidant also present at 0.01%.

Yet further examples 1C-7C are in accordance with the constituents of Examples 1–7 above with BHA antioxidant also present at 0.01%w/v and phenol at 0.25% w/v.

The formulations of the invention can be administered in a way appropriate to the specific use envisaged, the particular species and weight of host animal being treated, the parasite or parasites involved, degree of infestation, etc., according to standard medical and veterinary practice. Preferably the formulations according to the invention are administered by subcutaneous injection using a suitable veterinary dosing device, such as an injection gun of the types available from such suppliers as NJ Phillips Injector, Instrument Supplies and Simcrotec. Choice of the injection device depends on a number of factors such as the viscosity of the formulation, capability to deliver a unit dose of active drug in field conditions, etc., and according to standard medical and veterinary practice.

To illustrate the invention, for treatment of ticks, nematodes, etc. in cattle, a dose of doramectin of between 0.2 and 1.5 mg/kg, preferably about 0.6 mg/kg body weight of the host animal can be given as a once per season dosing. A typical dosage regime for a 0.6mg/kg dose would be 1–3 ml of the formulation of Example 1 once per season per animal.

Of course there will be instances where higher or lower dosage ranges are indicated and such are within the scope of this invention.

It is to be understood that reference to treatment or therapy includes prevention, alleviation and cure of the condition or conditions caused by the parasite.

The efficacy of the formulations according to the invention is illustrated by the following. Four long-acting formulations of doramectin (DRM) were administered as single injectable doses of 0.6 mg/kg or 1.0 mg/kg, and evaluated over time against artificial infestations of the one-host cattle tick, *Boophilus microplus*, on cattle. Six Hereford-Shorthorn steers with no previous cattle tick exposure were used for each treatment group and six animals were included in the untreated group. Calves were infested with the Yeerongpilly-susceptible strain of cattle tick for 24 days prior to treatment and were allocated to treatment group on the basis of the number of 4.5–8mm-sized ticks per side. The five study groups were as follows: untreated (T1), 6% DRM in castor oil:ethyl oleate (40:60) at 0.6 mg/kg, 0.5 ml/50 kg (T2), 5% DRM in castor oil:ethyl oleate (40:60) at 1 mg/kg, 1 ml/50 kg (T3), 6% DRM in castor oil:ethyl oleate (60:40) at 0.6 mg/kg, 0.5 ml/50 kg (T4), 5% DRM in castor oil:ethyl oleate (60:40) at 1 mg/kg, 1 ml/50 kg (T5). Infestation rates were 5000 tick larvae on three days per week prior to treatment and 5000 larvae on two days per week post-treatment. Treatments were administered subcutaneously into the neck and efficacy was determined by the yield of engorged female ticks and viable egg production from treated and untreated cattle. There were no adverse drug reactions and no mortalities during the study. The results showed that >95% control of adult ticks was achieved for 45 days by T2, 70 days by T3, 46 days by T4, and 77 days by T5.

What is claimed is:

1. A formulation comprising:

doramectin at about 1–11% w/v in a solvent comprising castor oil at about 55–75% v/v and either
    (i) ethyl oleate at about 20–75% v/v; or
    (ii) fractionated coconut oil at about 20–75% v/v; and
    (iii) optional further auxiliaries.

2. A formulation according to claim 1 wherein the amount of doramectin is about 3–9% w/v.

3. A formulation according to claim 1 wherein the amount of doramectin is about 5–9% w/v.

4. A formulation according to claim 1 wherein the amount of doramectin is about 6% w/v.

5. A method of treatment of an infection caused by an endo- or ectoparasite by administration of an effective amount of a formulation according to claim 1.

6. A method of treatment of an infection caused by an endo- or ectoparasite by administration of an effective amount of a formulation according to claim 1 wherein the amount of doramectin is about 6% w/v.

* * * * *